United States Patent
Engelhardt et al.

(10) Patent No.: US 7,798,985 B2
(45) Date of Patent: Sep. 21, 2010

(54) VENSOUS BUBBLE TRAP

(75) Inventors: Ralf Engelhardt, Ofterdingen (DE);
Enno-Utz Kueper, Hechingen (DE);
Ulrich Haag, Bisingen (DE)

(73) Assignee: Maquet Cardiopulmonary AG, Hirrlingen (DE)

(*) Notice: Subject to any disclaimer, the term of this patent is extended or adjusted under 35 U.S.C. 154(b) by 12 days.

(21) Appl. No.: 11/908,224

(22) PCT Filed: Mar. 7, 2006

(86) PCT No.: PCT/EP2006/002049

§ 371 (c)(1),
(2), (4) Date: Sep. 10, 2007

(87) PCT Pub. No.: WO2006/094752

PCT Pub. Date: Sep. 14, 2006

(65) Prior Publication Data

US 2008/0171962 A1 Jul. 17, 2008

(30) Foreign Application Priority Data

Mar. 11, 2005 (DE) .................. 10 2005 011 740

(51) Int. Cl.
*A61M 37/00* (2006.01)
*A61M 1/00* (2006.01)
*B01D 53/22* (2006.01)
*B01D 19/00* (2006.01)
*B01D 35/00* (2006.01)

(52) U.S. Cl. .................. 604/6.09; 604/4.01; 422/44; 422/45; 95/46; 210/188; 210/472; 210/539; 210/436

(58) Field of Classification Search ............... 604/6.09, 604/122; 210/188, 472, 539, 436; 95/46
See application file for complete search history.

(56) References Cited

U.S. PATENT DOCUMENTS

| 3,827,562 | A | * | 8/1974 | Esmond ............... 210/304 |
| 4,368,118 | A | * | 1/1983 | Siposs ............... 210/136 |
| 4,622,132 | A | * | 11/1986 | Chupka ............... 209/725 |
| 4,737,139 | A | * | 4/1988 | Zupkas et al. ......... 604/6.09 |
| 4,919,802 | A | * | 4/1990 | Katsura ............... 422/44 |
| 4,932,987 | A | * | 6/1990 | Molina ............... 96/212 |
| 5,084,244 | A | * | 1/1992 | Muramoto ............ 422/46 |
| 5,158,533 | A | | 10/1992 | Strauss et al. |
| 5,192,439 | A | * | 3/1993 | Roth et al. ........... 210/485 |
| 5,462,669 | A | * | 10/1995 | Yeh ................... 210/703 |

(Continued)

FOREIGN PATENT DOCUMENTS

WO 96/00593 1/1996

(Continued)

*Primary Examiner*—Tatyana Zalukaeva
*Assistant Examiner*—Susan Su
(74) *Attorney, Agent, or Firm*—Michael J. Striker

(57) ABSTRACT

In a venous bubble trap (1), having a housing (2) to which fluid, in particular blood, can be delivered essentially tangentially via a fluid inlet (8) and from which fluid can be carried away via a fluid outlet (10), and having a filter device (3) located in the interior of the housing (2), the filter device (3) divides the housing interior into a prefilter region (5) and a postfilter region (6), and the postfilter region (6) surrounds the prefilter region (5) in at least some portions. As a result, air is reliably removed from the fluid.

10 Claims, 1 Drawing Sheet

U.S. PATENT DOCUMENTS

| | | | | |
|---|---|---|---|---|
| 5,618,425 | A * | 4/1997 | Mitamura et al. | 210/493.5 |
| 5,632,894 | A * | 5/1997 | White et al. | 210/436 |
| 5,651,765 | A * | 7/1997 | Haworth et al. | 604/6.09 |
| 5,782,791 | A * | 7/1998 | Peterson et al. | 604/4.01 |
| 5,800,721 | A * | 9/1998 | McBride | 210/806 |
| 5,849,186 | A * | 12/1998 | Raneri et al. | 210/315 |
| 6,123,519 | A * | 9/2000 | Kato et al. | 417/395 |
| 6,176,904 | B1 * | 1/2001 | Gupta | 96/209 |
| 6,267,926 | B1 * | 7/2001 | Reed et al. | 422/48 |
| 6,328,789 | B1 * | 12/2001 | Spranger | 96/179 |
| 6,451,257 | B1 * | 9/2002 | Flamer | 422/44 |
| 7,108,785 | B1 * | 9/2006 | Plechinger et al. | 210/188 |
| 2004/0009097 | A1 * | 1/2004 | Stringer et al. | 422/45 |
| 2004/0228760 | A1 * | 11/2004 | Stringer et al. | 422/44 |

FOREIGN PATENT DOCUMENTS

WO      98/17369      4/1998

* cited by examiner

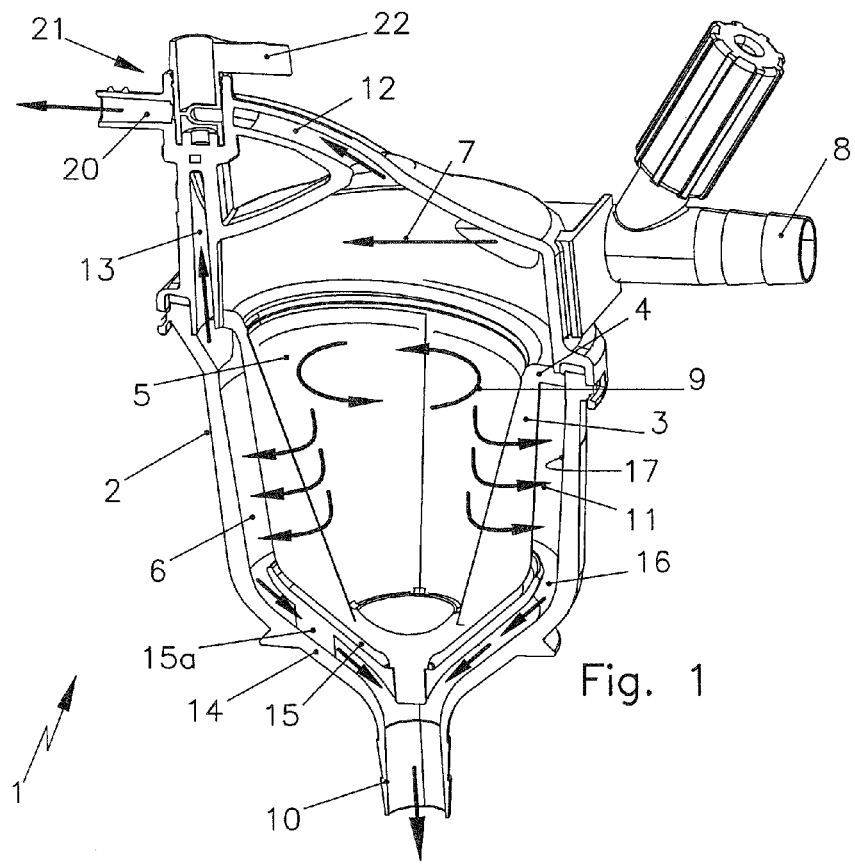
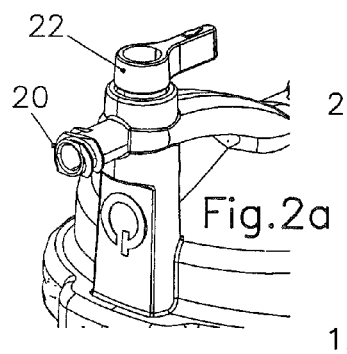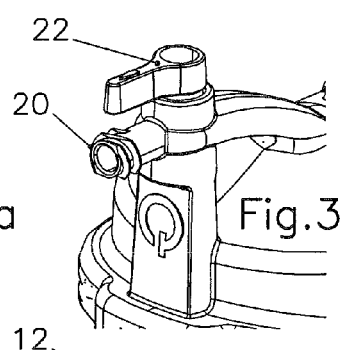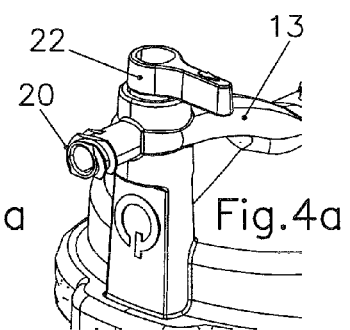
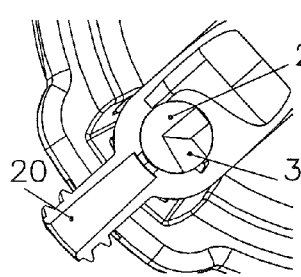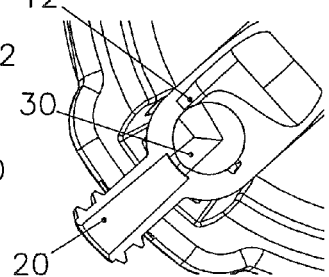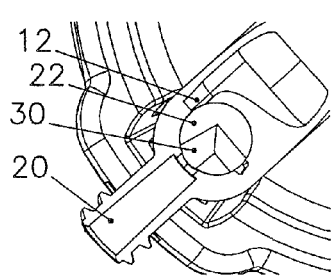

VENSOUS BUBBLE TRAP

The invention relates to a venous bubble trap, having a housing to which fluid, in particular blood, can be delivered essentially tangentially via a fluid inlet and from which fluid can be carried away via a fluid outlet, having a filter device located in the interior of the housing.

In various medical procedures, extracorporeal circulations are established, which means that blood is first pumped out of the patient's body via various medical products and then pumped back into the body. Great care must be taken to assure that no air or bubbles will re-enter the body with the blood.

In extracorporeal circulations, so-called bubble traps are provided, for eliminating air bubbles contained in the blood or other body fluids. One option is to place air bubble traps in the fluid line to the body. This is intended to assure that there are no longer any air bubbles immediately before the fluid enters the patient's body. In practice, it has been demonstrated that air bubbles can interfere with the function of devices in the extracorporeal circulatory system, in particular recirculating pumps. For instance, if air bubbles get into a blood pump, failure of the pump can even ensue, if there are large bubbles. Smaller air bubbles are broken apart by the pump into extremely fine microscopic bubbles, which can then neither be detected nor eliminated. These microscopic bubbles get into the patient's blood circulation, where they can cause embolisms in the organs.

It has therefore been proposed that bubble traps be located on the venous side. It is known, for concentrating air in the center of a filter or a bubble trap, to employ centrifuging. In centrifuging, the medium is set into rotation. The separation of the particles is effected by centrifugal force, based on the differences in density. The heavier a particle is (the higher its density is), the greater is the radius of the circular path in which it moves about the axis of rotation. Since tiny air bubbles have a lesser density than blood components, the bubbles collect in the center of the "eddy", and from there they can easily be removed.

In known venous bubble traps with a filter device located in the interior of the bubble trap, the rotating flow of blood through the filter medium is forced back into the interior of the bubble trap in the direction of the axis of rotation. The tiny air bubbles are pressed by centrifugal force inward against the filter medium, since they have the tendency to collect in the center of the rotating flow. As a result, the danger is great that the tiny bubbles can also be pressed inward through the filter cloth and thus into the outlet blood flow.

Moreover, if air enters the known venous bubble traps and then passes through the filter device, there is no possible way of venting the postfilter region in a targeted way.

The object of the present invention by comparison is to furnish a bubble trap with which a reliable separation of fluid and tiny air bubbles can be accomplished.

According to the invention, this object is attained in a manner that is as surprisingly simple as it is effective, in that the filter device divides the housing interior into a prefilter region and a postfilter region, and the postfilter region surrounds the prefilter region in at least some portions. Because of this provision, the fluid to be filtered is pressed from the inside outward through the filter device. In particular, the heavier fluid is forced outward through the filter device by the centrifugal force, while the lighter tiny air bubbles collect unimpeded in the center of the prefilter region and can be carried away directly from there. Hence the air is retained in the center of the "eddy". Therefore the air bubbles do not move on a circular path along the filter surface. Because the fluid is delivered to the bubble trap essentially tangentially, the fluid is set into a rotary motion in the interior of the bubble trap. A screen may be used as the filter device.

If the fluid inlet is located above the filter device, the fluid, given the greatest possible diameter of the housing interior, can be set unimpeded into a rotary motion.

In a preferred embodiment, the filter device has an edge that rests, in particular in sealing fashion, against the inner housing wall. As a result, the inner housing wall is subdivided into two partial chambers, and it is assured that unfiltered fluid cannot reach the postfilter region.

In a preferred feature of the invention, it is provided that the filter device tapers downward. Because of this cross-sectional reduction, the rotary speed of the fluid is increased. As a result, the centrifugal force increases with an increasing approach to the fluid outlet region.

It is especially advantageous if an outlet flow guide is provided in the fluid outlet region. This assures that the fluid, in particular blood, is aspirated away as close as possible to the inner housing wall. The outlet flow guide promotes the ascension of bubbles in the postfilter region. If it were not present, then any bubbles that pass through the filter device would arrive directly at the fluid outlet.

If the outlet flow guide is spaced apart by a gap from the inner housing wall, then fluid can get into the fluid outlet only via this gap. This means that only fluid that is located at a distance from the filter device, in particular fluid that is located in the vicinity of the inner housing wall, can leave the bubble trap.

In an especially preferred variant of the invention, it is provided that the outlet flow guide is spaced apart from the bottom of the housing via one or more spacers. This means that fluid must first flow some distance between the bottom of the housing and the outlet flow guide, before it leaves the bubble trap. Between the outlet flow guide and the bottom of the housing, a kind of conduit is formed.

In a feature of the invention, it may be provided that the prefilter region and the postfilter region are separately ventable. This has the advantage that air or bubbles need not be pressed through the filter device in order to be capable of being removed, since air from both regions of the housing can be removed separately. If tiny air bubbles unintentionally enter the postfilter region, for instance because the maximum retention volume has been exceeded, then they once again have the opportunity there of ascending and being removed through the second venting conduit.

The separate ventability can be implemented especially simply if a first venting conduit is provided for the prefilter region and a second venting conduit, separate from the first, is provide for the postfilter region.

The number of connections and hence the costs of the bubble trap can be kept low if the first and second venting conduits have a common blocking device and a common venting conduit. In particular, the venting of the two regions can be effected separately via a commonly used Luer port and a commonly used spigot as a blocking device.

Preferably, the blocking device has three functional positions. In a first position, the prefilter region and postfilter region are closed off from the common venting conduit. In a second position, only the first venting conduit is opened, and in a third position, only the second venting conduit is opened.

Further characteristics and advantages of the invention will become apparent from the ensuing detailed description of an exemplary embodiment of the invention, in conjunction with the drawing figures, which show details essential to the invention, and from the claims. The individual characteristics may each be realized individually on their own or a plurality of them may be combined arbitrarily in variants of the invention.

In the schematic drawings, one exemplary embodiment of the invention is shown, which is described in detail in the ensuing description.

Shown are:

FIG. 1, a sectional view of a bubble trap of the invention;

FIG. 2a, a portion of the bubble trap with a first position of a blocking device;

FIG. 2b, a sectional view through the blocking device in the position shown in FIG. 2a;

FIG. 3a, a portion of the bubble trap with a second position of a blocking device;

FIG. 3b, a sectional view through the blocking device in the position shown in FIG. 3a;

FIG. 4a, a portion of the bubble trap with a third position of a blocking device;

FIG. 4b, a sectional view through the blocking device in the position shown in FIG. 4a.

In FIG. 1, a sectional view of a bubble trap 1 for use in an extracorporeal circulatory system is shown. Located in a housing 2 is a filter device 3, which subdivides the interior of the housing 2 into a prefilter region 5 and a postfilter region 6; the postfilter region 6 partly surrounds the prefilter region 5. The filter device 3 has an edge 4, which seals off the filter device from the housing 2. Fluid can therefore pass from the prefilter to the postfilter region only through the filter device 3.

In the prefilter region 5, above the filter device 3, fluid is delivered to the housing 2 substantially tangentially, which is indicated by the arrow 7. The fluid is delivered via a fluid inlet 8. The inlet 8 is located so that it extends over a tangent to a housing wall and hereby delivers the fluid off the housing axis directly to the housing wall substantially tangentially to the latter. Because of the essentially tangential delivery of the fluid, the fluid is set in the interior of the housing 2 into a rotary motion, which is indicated by the arrows 9. The filter device 3 tapers toward the fluid outlet 10.

Because of the centrifugal force, fluid from the prefilter region 5 is forced through the filter device 3 into the postfilter region 6, as indicated by the arrows 11. In the center of the filter device 30, air bubbles collect, which rise upward and can be removed from the prefilter region 5 through a first venting conduit 12. If air from the prefilter region 5 nevertheless enters the postfilter region 6, this air can escape via the second venting conduit 13.

In the vicinity of the bottom 14 of the housing 2, an outlet flow guide 15 is provided, which is spaced apart from the bottom 14 via spacers 15a. Between the outlet flow guide 15 and the bottom 14, a conduit is formed, through which fluid can flow out from the postfilter region 6. The outlet flow guide 15 is spaced apart by a gap 16 from the inner housing wall 17, so that fluid is forced to flow out of the region of the inner housing wall 17, or in other words out of a region that is at a distance from the filter device 3, so that after passing through the filter device 3, the fluid must travel a certain distance before it can escape from the housing 2. Because the fluid must travel this distance, any tiny bubbles passing through the filter device 3 have enough time to become separated from the fluid and to rise.

The venting conduits 12, 13 have a common venting conduit 20, with which they communicate via a Luer port 21. The Luer port 21 has a blocking device 22, through which the first venting conduit 12 or the second venting conduit 13 can communicate with the common venting conduit 20.

In FIG. 2a, the blocking device 22 is shown in a closed position. This means that neither of the venting conduits 12, 13 is in communication with the common venting conduit 20 via the blocking device 22. This is shown clearly in the sectional view of FIG. 2b. The blocking device 22 has a conduit 30, which in the position of the blocking device 22 as shown is not in communication with the common venting conduit 20.

In FIG. 3a, the blocking device 22 is in a second functional position, in which the common venting conduit 20 is in communication with the first venting conduit 12. This becomes especially clear from the view in FIG. 3b, where the conduit 30 is in communication with the first venting conduit 12 and with the common venting conduit 20. The second venting conduit 13 is not in communication with the venting conduit 20.

In FIG. 4a, the blocking device 22 is shown in a third functional position, in which the common venting conduit 20 is in communication with the second venting conduit 13 through the conduit 30. As seen from FIG. 4b, the first venting conduit 12 is not in communication with the venting conduit 20. FIGS. 2b, 3b and 4b make it clear that because of the design of the blocking device 22, the first and second venting conduits 12, 13 cannot both simultaneously communicate fluidically with the common venting conduit 20. Separate venting of the prefilter region and of the postfilter region is thus assured.

The invention claimed is:

1. A venous bubble trap (1), comprising a housing (2) having an axis; a fluid inlet (8) delivering a fluid into an interior of the housing (2); a fluid outlet (10) via which the fluid is carried away; a filter device (3) located in the interior of the housing (2), and dividing the housing interior into a pre-filter region (5) and a post-filter region (6), with the post-filter region (6) surrounding the pre-filter region (5) in at least some portions, wherein the inlet (8) is located so that it extends substantially over a tangent to a housing wall off the housing axis and thereby delivers the fluid off the housing axis directly toward the housing wall, causes a rotating motion in the fluid and results in a centrifugal force that causes bubbles to gather in a center of the rotating fluid, and wherein the filter device (3) tapers downward toward the fluid outlet (10) and has a filter inlet at the upper wider end through which the fluid flows into an interior of the downwardly tapering filter device and a lower narrower end, thus increasing a rotational velocity of the fluid and a bubble separation from the latter.

2. The bubble trap as defined by claim 1, wherein the fluid inlet (8) is located above the filter device (3).

3. The bubble trap as defined by claim 1, wherein the filter device (3) has an edge (4) that rests on the inner housing wall.

4. The bubble trap as defined by claim 1, further comprising, an outlet flow guide (15) provided in a fluid outlet region.

5. The bubble trap as defined by claim 4, wherein the outlet flow guide (15) is spaced apart by a gap (16) from an inner housing wall (17).

6. The bubble trap as defined by claim 4, wherein the outlet flow guide (15) is spaced apart via one or more spacers (15a) from a bottom (14) of the housing (2).

7. The bubble trap as defined by claim 1, wherein the pre-filter region (5) and the postfilter region (6) are separately ventable.

8. The bubble trap as defined by claim 7, wherein a first venting conduit (12) is provided for the prefilter region (5), and a second venting conduit (13), separate from the first venting conduit, is provided for the postfilter region (6).

9. The bubble trap as defined by claim 8, wherein the first and second venting conduits (12, 13) have a common blocking device (22) and a common venting conduit (20).

10. The bubble trap as defined by claim 9, wherein the blocking device (22) has three functional positions.

* * * * *